(12) United States Patent
Feldman et al.

(10) Patent No.: US 7,238,199 B2
(45) Date of Patent: Jul. 3, 2007

(54) METHOD AND APPARATUS FOR STENT DEPLOYMENT WITH ENHANCED DELIVERY OF BIOACTIVE AGENTS

(75) Inventors: Marc D. Feldman, San Antonio, TX (US); Stephen R. Bailey, San Antonio, TX (US); C. Mauli Agrawal, San Antonio, TX (US); Kyriacos A. Athanasiou, Houston, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 143 days.

(21) Appl. No.: 10/469,632

(22) PCT Filed: Feb. 27, 2002

(86) PCT No.: PCT/US02/05782

§ 371 (c)(1),
(2), (4) Date: Aug. 29, 2003

(87) PCT Pub. No.: WO02/069848

PCT Pub. Date: Sep. 12, 2002

(65) Prior Publication Data

US 2005/0171595 A1    Aug. 4, 2005

Related U.S. Application Data

(60) Provisional application No. 60/273,592, filed on Mar. 6, 2001.

(51) Int. Cl.
*A61F 2/06* (2006.01)

(52) U.S. Cl. .................. 623/1.15; 623/1.39; 623/1.42; 623/1.46

(58) Field of Classification Search ............... 623/1.15, 623/1.39, 1.4, 1.42, 1.43, 1.46
See application file for complete search history.

(56) References Cited

U.S. PATENT DOCUMENTS

| | | | |
|---|---|---|---|
| 5,197,977 A | 3/1993 | Hoffman, Jr. et al. | 623/1 |
| 5,282,847 A | 2/1994 | Trescony et al. | 623/1 |
| 5,380,299 A | 1/1995 | Fearnot et al. | 604/265 |
| 5,383,927 A | 1/1995 | De Goicoechea et al. | 623/1 |
| 5,464,450 A | 11/1995 | Buscemi et al. | 623/6 |
| 5,500,013 A | 3/1996 | Buscemi et al. | 623/1 |
| 5,607,464 A | 3/1997 | Trescony et al. | 623/1 |
| 5,624,411 A | 4/1997 | Tuch | 604/28 |
| 5,653,745 A | 8/1997 | Trescony et al. | 623/1 |
| 5,769,883 A | 6/1998 | Buscemi et al. | 623/1 |
| 5,776,184 A | 7/1998 | Tuch | 623/1 |
| 5,873,904 A * | 2/1999 | Ragheb et al. | 623/1.13 |
| 5,954,706 A | 9/1999 | Sahatjian | 604/509 |
| 5,980,551 A | 11/1999 | Summers et al. | 606/194 |
| 5,980,564 A | 11/1999 | Stinson | 623/1 |

(Continued)

FOREIGN PATENT DOCUMENTS

WO    WO 9823228 A1 *  6/1998

*Primary Examiner*—Corrine McDermott
*Assistant Examiner*—Thomas J. Sweet
(74) *Attorney, Agent, or Firm*—Robert W Strozier

(57) ABSTRACT

A stent for use in animals including humans is disclosed which includes unprotected and protected regions, each protected regions including a bioactive or biopenetrating agent containing therein where the protected regions are protected by the unprotected regions when the stent is in its undeployed state which has a smaller cross-sectional dimension than the stent in its deployed state. And when the stent is in its deployed state the bioactive or biopenetrating agent(s) are brought into direct and intimate contact with a tissue or interior of a blood vessel of an animal including a human.

22 Claims, 11 Drawing Sheets

U.S. PATENT DOCUMENTS

| | | | |
|---|---|---|---|
| 5,985,307 A | 11/1999 | Hanson et al. | 424/423 |
| 6,001,117 A | 12/1999 | Huxel et al. | 606/191 |
| 6,001,123 A | 12/1999 | Lau | 623/1 |
| 6,017,362 A * | 1/2000 | Lau | 623/1.2 |
| 6,071,305 A * | 6/2000 | Brown et al. | 623/1.43 |
| 6,080,190 A | 6/2000 | Schwartz | 623/1 |
| 6,165,210 A | 12/2000 | Lau et al. | 623/1.12 |
| 6,254,628 B1 * | 7/2001 | Wallace et al. | 623/1.12 |
| 6,273,913 B1 * | 8/2001 | Wright et al. | 623/1.42 |

* cited by examiner

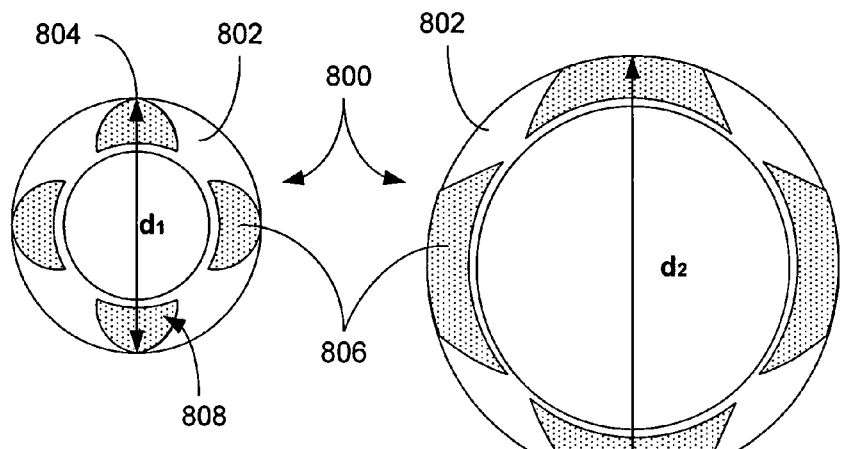
FIG. 8A
FIG. 8B
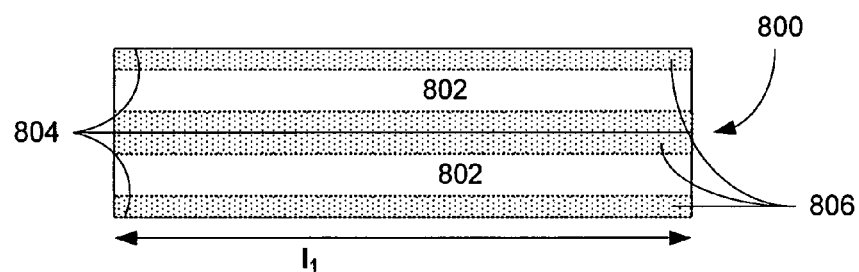
FIG. 8C
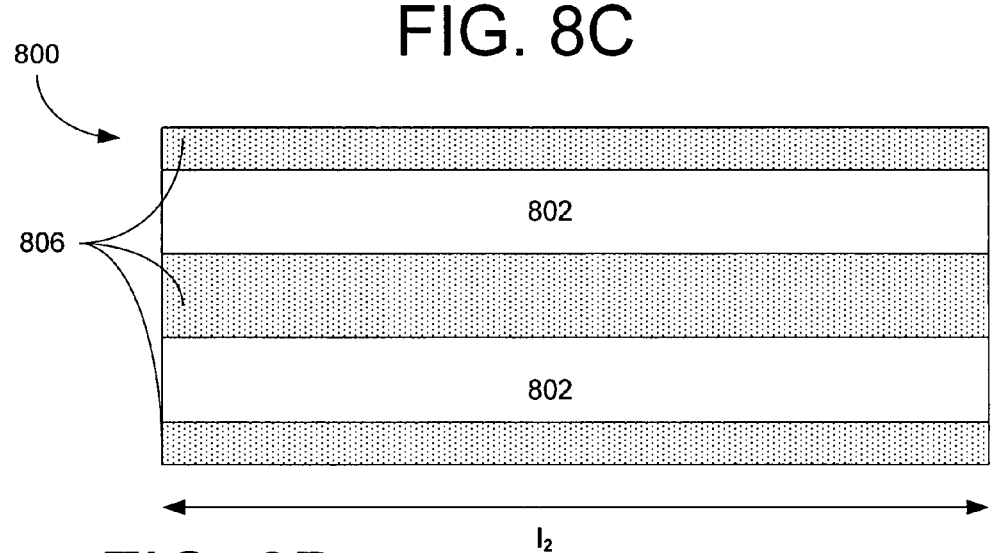
FIG. 8D

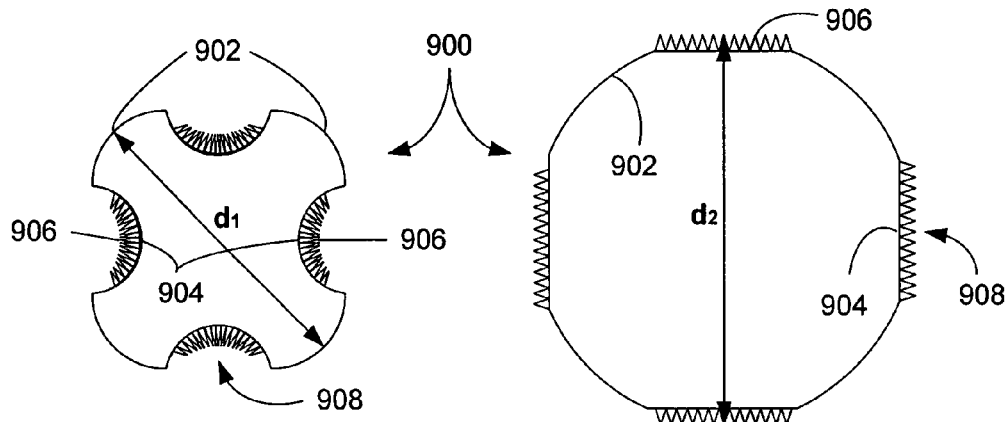
FIG. 9A
FIG. 9B
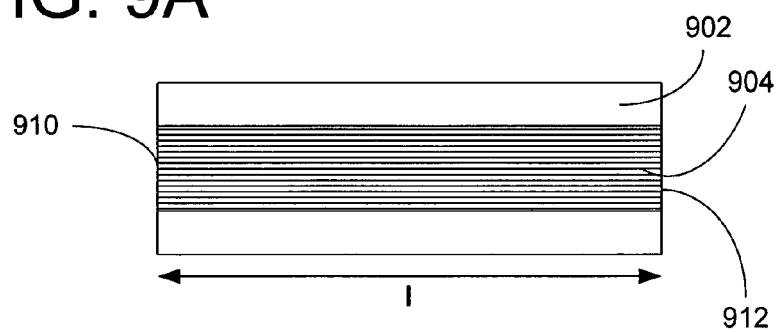
FIG. 9C
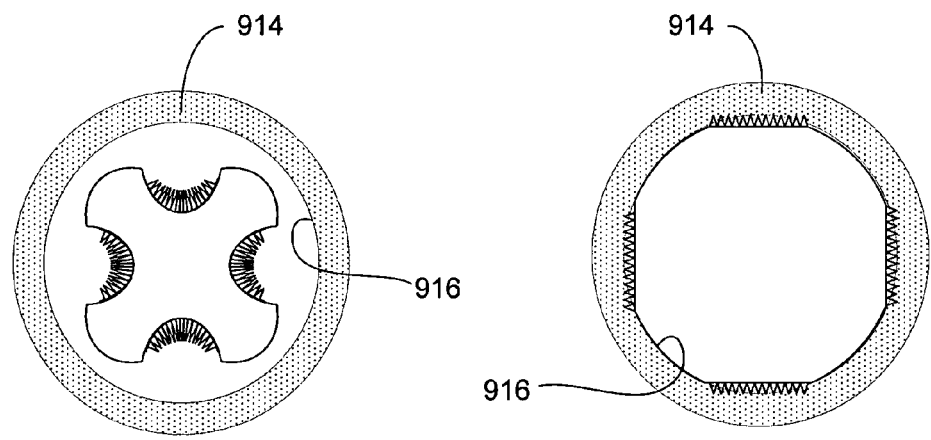
FIG. 9D
FIG. 9E

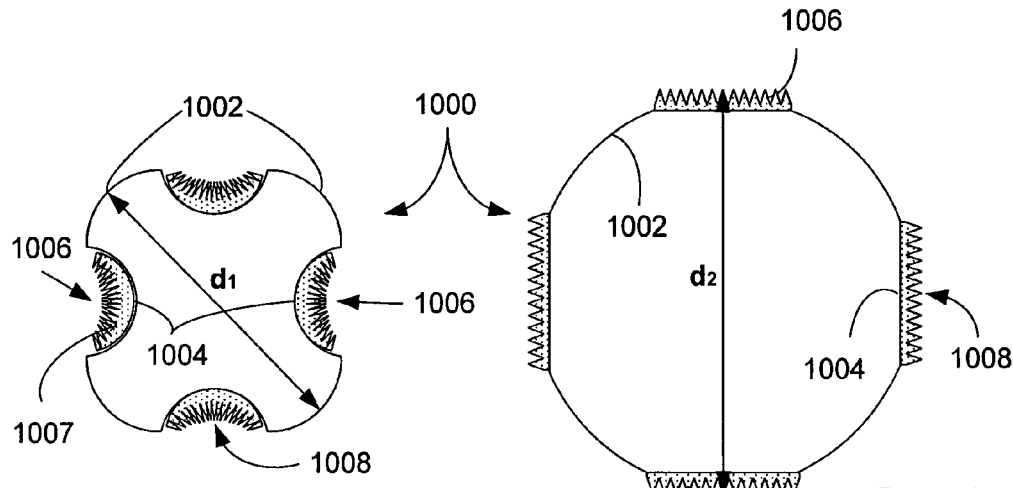
FIG. 10A
FIG. 10B
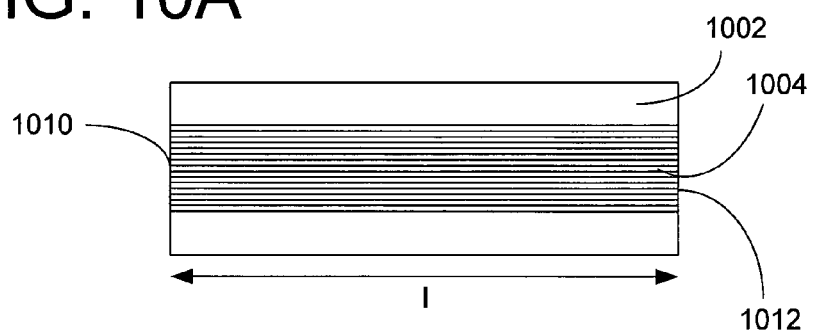
FIG. 10C
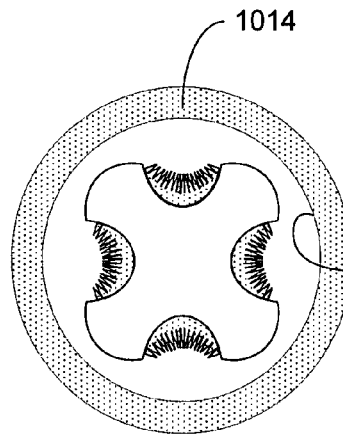
FIG. 10D
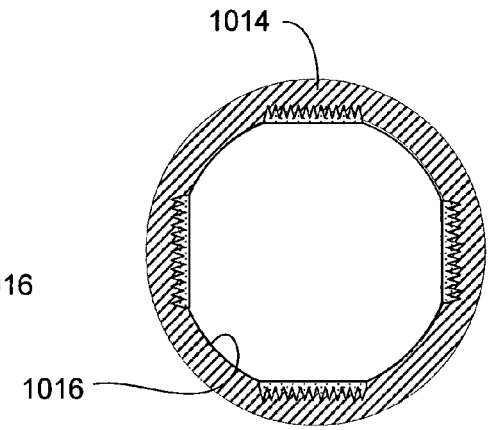
FIG. 10E

METHOD AND APPARATUS FOR STENT DEPLOYMENT WITH ENHANCED DELIVERY OF BIOACTIVE AGENTS

RELATED APPLICATIONS

This application is a 35 U.S.C. § 371 National Phase Application of PCT/US02/05782 filed 27 Feb. 2002, which claims provisional priority to U.S. Provisional Patent Application Ser. No. 60/273,592 filed 6 Mar. 2001.

BACKGROUND OF THE INVENTION

1. Field of the Invention

This invention relates to a stent including indentations having either bioactive agents and/or penetrating structures and/or agents therein or thereon where the indentations protect the agents or structures during stent positioning and where the agents or structures are brought into close proximity to or in contact with a vessel's interior or tissue during stent deployment.

More particularly, this invention relates to a corrugated stent having recessed regions containing bioactive or penetration agents or structures and non-recessed regions, where the agents are protected in the recessed regions. Preferably, the stent undergo a volumeric expansion after deployment, that brings the bioactive or penetration agents or structures into close proximity to or direct contact with a a vessel's interior or tissue during deployment.

2. Description of the Related Art

Stents are a valuable medical device designed to maintain pathway of a vessel or maintain or create a tissue cavity in an animal's body in an opened condition. Numerous stents have been described such as those in U.S. Pat. Nos. 5,197,977, 5,282,847, 5,380,299, 5,383,927, 5,464,450, 5,500,013, 5,607,464, 5,624,411, 5,653,745, 5,769,8835, and 5,776,184, incorporated herein by reference. However, these stents lack bioactive or penetrating agents to assist in vessel or tissue healing or deposit digestion, and/or mechanisms for the protection of bioactive or penetrating agents during stent deployment and positioning.

Thus, there is a need in the art for an improved stent having bioactive or penetrating agents deposited thereon in such a way as to protect the agents during deployment and placement and capable of bringing the agents into close proximity or direct contact with a vessel's and/or tissue interior after deployment and expansion.

SUMMARY OF THE INVENTION

The present invention provides stents for treating, expanding and/or supporting a portion of a vessel or for treating a tissue site, when the stent is inserted into the vessel or tissue site. The stents include at least one or one or more recessed region and at least one or one or more non-recessed region. One or more of the recessed regions can contain: 1) a bioactive composition designed to chemically or biochemically interact with the interior of the vessel or the tissue site to cause a prophylactic and/or therapeutic effect; 2) a penetrating apparatus or structure designed to mechanically or physically interact with the interior of the vessel or the tissue site to cause a prophylactic and/or therapeutic effect; or 3) a mixture or combination thereof. The stents have a deployed and non-deployed state that can be the same or different. In the deployed state, the recessed regions can remain recessed, become essentially flush with the non-recessed regions, protrude above the non-recessed regions and/or include portions that remain recessed relative to the non-recessed regions, protrude above the non-recessed regions or are essentially flush with the non-recessed regions. The term essentially flush means that in the deployed state, the non-recessed and recessed regions form an essentially continuous surface.

In one preferred embodiment, the stents of the present invention do not change shape after deployment. In another preferred embodiment, the stents of the present invention have an expanded or deployed state and non-expanded or non-deployed state. In the non-expanded or non-deployed state, the stent has a smaller dimension compared to the stent in its expanded or deployed state. The dimension can be a cross-sectional dimension, a length dimension or a combination thereof. When the stent is in its non-expanded or non-deployed state, the non-recessed regions protrude or extend above and protect the compositions and/or structures contained in the recessed regions.

Moreover, the non-recessed regions are designed to deform, expand and/or elongate to a lesser extent during stent expansion or deployment than the recessed regions. On the other hand, the recessed regions are designed to deform, expand, elongate and/or flatten during deployment. The deformation of the recessed regions during stent deployment can cause the stent to assume a final contour, where the recessed regions are substantially continuous with the non-recessed regions so the all portion of the deployed stent contact the tissue site or surface to approximately the same extent. Alternatively, the stent can deploy so that the recessed regions extend above the non-recessed regions contacting the tissue site or surface to a greater extent than the non-recessed regions. This deformation serves to bring the compositions, structures or combinations or mixtures thereof situated in the recessed regions into close proximity or direct contact with the tissue surface such as the interior of a vessel or the tissue within a tissue site at the site of deployment.

The present invention also provides bioerodible stents of the present invention having the same attributes of the stents disclosed above with the added attribute that the stents themselves will eventually degrade, dissolve, erode, be metabolized or otherwise be gradually removed from the site of implantation.

The present invention also provides a method for treating, expanding or supporting a vessel or other tissue site to achieve a given prophylactic or therapeutic result including the step of positioning a stent of the present invention at a desired site or position in an interior of a vessel or within a tissue in the body of an animal. Once properly positioned, the stent is expanded or deployed forcing the recessed regions to deform, expand, elongate and/or flatten. The deformation of the stent can cause the non-recessed regions and recessed regions to be brought into close proximity or direct contact with the tissue site exposing the tissue site to the compositions and/or structures contained within the recessed regions. Alternatively, the deformation can cause the recessed regions to protrude or extent above the non-recessed regions so that the compositions and/or structures contained within the recessed regions contact the tissue site to a greater extent than the non-recessed region. An ordinary artisan should realized that in this embodiment, the recessed regions in the non-deployed state have become the non-recessed regions of the deployed states and vis-a-versa. The contact between the stent recessed regions and the tissue site produce a therapeutic and/or prophylactic effect. If the stent is bioerodible, an additional step will be the gradual removal or decomposition of stent itself.

The present invention also provides a method for treating, expanding or supporting a tissue site to achieve a given prophylactic and/or therapeutic result which includes positioning a stent of the present invention at a desired site or position in a tissue of the body of an animal including a human. Once properly positioned, the stent is deployed, thereby forcing the recessed regions to deform, expand, elongate and/or flatten. The deformation of the stent can cause the non-recessed regions and recessed regions to be brought into close proximity or direct contact with the tissue site exposing the tissue site to the compositions and/or structures contained within the recessed regions. Alternatively, the deformation can cause the recessed regions to protrude or extent above the non-recessed regions so that the compositions and/or structures contained within the recessed regions contact the tissue site to a greater extent than the non-recessed region. An ordinary artisan should realize that in this embodiment, the recessed regions in the non-deployed state have become the non-recessed regions of the deployed states and vis-a-versa. The contact between the stent recessed regions and the tissue site produce a therapeutic and/or prophylactic effect. If the stent is bioerodible, an additional step will be the gradual removal or decomposition of stent itself.

The present invention further provides methods for making the stents of the present invention.

DESCRIPTION OF THE DRAWINGS

The invention can be better understood with reference to the following detailed description together with the appended illustrative drawings in which like elements are numbered the same:

FIG. 8A is a radial cross-sectional view of a eight preferred embodiment of a stent of the present invention in it undeployed state;

FIG. 8B is a side view of the stent of FIG. 8A in its deployed state;

FIG. 8C is a side view of the stent of FIG. 8A in its undeployed state;

FIG. 8D is a side view of the stent of FIG. 8B in its deployed state;

FIG. 9A is a radial cross-sectional view of a ninth preferred embodiment of a stent of the present invention in its undeployed state;

FIG. 9B is a radial cross-sectional view of the stent of FIG. 9A in its deployed state;

FIG. 9C is a side view of the stent of FIG. 9A in its deployed state;

FIG. 9D is a radial cross-sectional view the stent of FIG. 9A in its undeployed state positioned within a blood vessel;

FIG. 9E is a radial cross-sectional view the stent of FIG. 9A in its deployed state now engaging an interior of the blood vessel;

FIG. 10A is a radial cross-sectional view of a ninth preferred embodiment of a stent of the present invention in its undeployed state;

FIG. 10B is a radial cross-sectional view of the stent of FIG. 10A in its deployed state;

FIG. 10C is a side view of the stent of FIG. 10A in its deployed state;

FIG. 10D is a radial cross-sectional view the stent of FIG. 10A in its undeployed state positioned within a blood vessel; and FIG. 10E is a radial cross-sectional view the stent of FIG. 10A in its deployed state now engaging an interior of the blood vessel.

DEFINITIONS

Figures 1A, 1B:
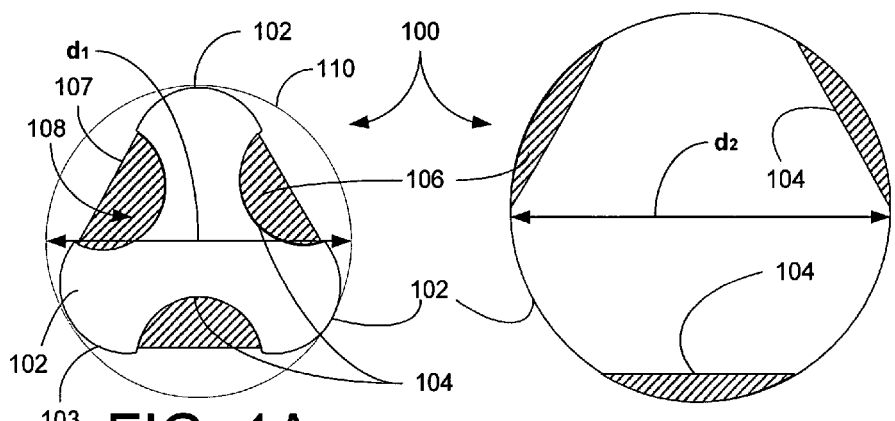
FIG. 1A is a radial cross-sectional view of a first preferred embodiment of a stent of the present invention in its undeployed state.
FIG. 1B is a radial cross-sectional view of the stent of FIG. 1A in its deployed state.

The term vessel means any vessel or vessel like structure in an animal (including humans) including, without limitation, ureter, airways, pancreatic ducts, biliary ducts, lymphatics, arteries, veins or other vessel type structures in the body.

The term animal means any organism that is a member of the animal kingdom including, without limitation, mammals including humans.

The term gradient means a change in some property over a given cross-section of a composition or article. The property can be, without limitation, the concentration of one or more compounds, physical structures, compositional make-up, permeability, porosity, or any other property of a composition or a structure. A gradient can vary smoothly, can includes one or more peaks, can be vary continuously, discretely or discontinuously across a given cross-section. A gradient peaks when the property has relative maxima in specific regions of the composition or structure across some cross-section.

DETAILED DESCRIPTION OF THE INVENTION

The inventors have found that a stent can be constructed that, in its undeployed state, include at least one zone, region, volume or area that protects something deposited in or on, contained in or on, or affixed to or within, positioned in or on, such as, without limitations, bioactive agents or compositions, penetration structures and/or mixtures or combination thereof at least one recessed region of the stent. The compositions and/or structures lie below and are protected by at least one non-recessed region of the stent so that during deployment the compositions and/or structures are protected against contact with the deployment tools or the interior of vessels or tissue sites prior to being properly positioned for final deployment.

Generally, deployment involves dimensional or volumetric expansion of the stent at its site of deployment in a body such as in a vessel or tissue site. The dimensional or volumetric expansion can occur in both the non-recessed and recessed regions to the same or different extent. In a preferred embodiment, the expansion occurs primarily in the recessed regions. The expansion can be radial, axial or a combination of radial and axial. In preferred embodiments, the expansion occurs substantially radial or substantially axial. The expansion causes the recessed regions to become accessible and/or more accessible to the site of deployment so that, in the final stent shape, the composition and/or structures are brought in close proximity to or into direct contact with the site of deployment. The proximity or contact allows the compositions and/or the structures to impart the desired prophylactic and/or therapeutic effect at the site of deployment.

Broadly, the stents of the present invention have an elongate shape, i.e., the stents generally have an axial dimension that is greater then their radial dimension. One unique feature of the stents of the present invention are the presence of at least one recessed region and one non-recessed region in the stent in its non-deployed state that forms a protected zone or volume in which composition and/or structures can be introduced that will impart a desired prophylactic and/or therapeutic effect at the site of deployment. Preferably, the stent includes a plurality of recessed, non-recessed regions and a plurality of protected regions, zones, areas or volumes into which composition and/or structures can be introduced that will impart a desired prophylactic and/or therapeutic effect to a site of deployment after stent deployment. The recessed and non-recessed regions of the stent form protected zones in the stent. These zone can extend radially, axially or mixtures or combinations of radial or axial zones. The zones are designed to be filled with or contain bio-active compositions and/or structures. The compositions and/or structures can be, without limitation, affixed to the stent in the zones, formed in the zones, deposited in the zones, contained in the zones, or mixtures or combinations thereof.

The stents also have a non-deployed and deployed state, where an overall shape of the stents changes when transitioning from its non-deployed to its deployed state resulting in the deprotection and/or exposure of the compositions and/or structure situated within the recessed regions of the stent. Generally, the shape change involves a volumetric expansion of the stents after deployment, i.e., the volume of the stent in its non-deployed state is smaller than its volume in its deployed state. If the change in volume is primarily due to a radial expansion of the stent, then the radial cross-sectional area of the stent in its non-deployed state is less than its deployed radial cross-sectional area. If the change in volume is primarily due to an axial expansion (elongation), then the length of the stent in its non-deployed state is less than its length in its deployed state. And if the stent expands both radially and axially, then its radial cross-sectional area and length both increase after deployment. However, the stents can also be constructed so that their volume or overall shape remains substantially the same, except that the non-recessed regions of the non-deployed stent become the recessed regions of the deployed stent and vis-a-versa.

In one preferred embodiment, the non-recessed regions are more rigid and non-deformable than the recessed regions of the stent. In this preferred configuration, the non-recessed regions substantially maintain their shape during stent expansion; while the recessed regions undergo deformation sufficient to deprotect the compositions and/or structures situated within the protected zones allowing the bio-active compositions and/or structures to affect their prophylactic and/or therapeutic effect at the site of deployment after deployment. One simple manufacture process for imparting differential deformation resistances to the recessed and non-recessed regions of a stent is to make the stent thicker at the non-recessed regions than at the recessed regions.

Broadly, the method of deployment of the stents of the present invention includes positioning a stent of the present invention at a desired site in a body of an animal in its non-deployed state and deploying the stent at the site, where deployment causes the stent to undergo a volumetric expansion bringing the compositions and/or structures within the protected regions or zones in close proximity to or into direct contact with the site. If the stent is to be deployed in a vessel, then the method includes forming an opening in the vessel, positioning the stent within the vessel at a desired site, and deploying the stent at that site. If the stent is to be deployed in a tissue or organ, then the method includes forming an opening in the tissue or organ, positioning the stent within the tissue or organ at a desired site, and deploying the stent at that site. Alternatively, the stent can simply be inserted into the tissue or tissue site and deployed. Generally, the stent is first placed or positioned in a medical instrument which maintains the stent in its non-deployed state and allows for positioning of the stent at a desired site within a vessel, tissue or organ of an animal body. One preferred embodiment of this invention relates to an elongated structure having a corrugated radial cross-section including axially disposed peaks (non-recessed regions) and valleys (recessed regions), where the valleys are filled with the compositions and/or structures to a position below the tops of the peaks. Another preferred embodiment includes an elongated structure having a pleated radial cross-section including axially disposed peaks and valleys, where the valleys are filled with the compositions and/or structures to a position below the tops of the peaks. In these two embodiments, the peaks and valleys can be disposed in a purely axial fashion or the structure can be twisted so that the peaks and valleys can appear as helices.

Another preferred embodiment includes an elongated structure having peaks and valleys disposed radially, where the valleys are filled with the compositions and/or structures to a position below the tops of the peaks.

Another preferred embodiment includes an elongated structure that is under tension in its non-deployed state and relaxed in its deployed state, such that the bioactive composition and/or structures are substantially hidden in the non-deployed state and accessible in the deployed state. In this latter embodiment, the hidden or protected regions or zones can be disposed axially or radially.

Moreover, the stent itself can degrade and eventually disappear.

In any embodiment, composition including bioactive agents and/or structure including penetrating agents can be situated in the protected zones of the stent. The compositions and/or structures can be situated within the protected regions by, without limitation, coating, adhering, forming, extruding, dipping, deposited in the protected zones. The protected zones or regions can be, without limitation, indentations, valleys, pockets, or the like or mixtures combination thereof. As the stent is inserted inside a vessel, tissue site or organ, these recessed or protected regions are shielded from mechanical removal, abrasion or rubbing due to contact with the vessel(s) and/or tissue during delivery. For use in the heart, the stents are generally delivered via the femoral artery, and normally must traverse plaque laden coronary arteries before they reach the site of deployment. Thus, by placing or situating the bioactive compositions and/or structures within the protected regions of the stent, but below the non-recessed regions of the stent or in regions hidden in the non-deployed state, the loss of bioactive compositions and/or structures during deployment is reduced and an improved delivery of bioactive compositions and/or structures to the site of treatment is achieved.

Once the site of treatment or deployment is reached, the stent is deployed and assumes its deployed shape which may involve a volumetric expansion, radial and/or axial, or simply a change in the regions of the stent that are exposed and accessible. If the stent undergoes a volumetric expansion, then such an expansion can occur in all regions of the stent to the same or different extent or can occur primarily in the recessed regions. Regardless, of the final deployed shape of the stent, the final shape or state exposes or further exposes the compositions and/or structures situated in the recessed and brings them in close proximity to or into direct contact with the vessel interior or the tissue at the site of deployment. The penetrating agents or structures are designed to cut, abrade, serrate, break, perforate, puncture and/or penetrate a vessel wall, a plaque deposit in a vessel, a desired structure within a tissue, a tumor, a cyst, or other structure within the body of an animal. The structures can also be designed to dislodge, dissolve, remove and/or eliminated a desired structure within the body of an animal. Examples of penetrating agents can include plaque dissolving chemicals (e.g., collegenase, elastase, etc.), and mechanical structures (e.g., metal, plastic, bioerodible polymers, micro or nano electromechanical systems, device or apparatus, nano-structures with biological effects, chemical effects, mechanical effects, electrical effects or mixtures thereof, etc.) situated in the protected regions of the stent or mounted within the protected regions of the stent. If the structure is an electromechanical apparatus, system or device, then the structure could undergo oscillatory motion allowing the structure to abrade or grind away a structure such as a plaque deposit. The oscillatory motion could be powered by an internal power source or the structure could include an antenna for absorbing power from an external field similar to the manner in which passive tagging devices are made as described in U.S. Pat. Nos. 6,192,279; 6,120,460; and 5,820,589, incorporated herein by reference with respect to the electronics needed for external field activation of a remote electromechanical device. If the structure includes an electric field alignable microcrystals such as crystals used in piezoelectric transducers, an oscillatory electric field would cause the crystals to undergo an oscillatory motion to grind or abrade a given structure in the body such as a plaque deposit. The electric field could also cause movement of DNA or proteins off the stent into the tissue since DNA and proteins are charged structures. Of course, because electric and magnetic fields are coupled mathematically by Maxwell's equations, magnetic fields can also be used.

One preferred agent delivery system involves the use of encapsulated plaque dissolving chemicals. Upon stent deployment, the capsules are designed to rupture and deposit the agents onto the plaque. Another embodiment involves the use of metal or biodegradable structures to penetrate the plaque. These plaque penetrating structures preferably have a profile smaller than the height of the non-recessed areas of the stent and are generally situated in the protected zone near a center of the recessed regions. After deployment, the structures generally extend above the non-recessed regions of the stent so that the structures have a greater opportunity to directly contact or protrude into the plaque. The penetrating structures may be microporous so that the structure can contain drugs, genes or other prophylactic and/or therapeutic agents and may be a micro or nano structures including micro and nano mechanical, electrical, electro-mechanical, etc. structures. Another embodiment involves the rapid or gradual release of bioactive agent (drugs, genes, growth factors and/or growth factor inhibitors) through the use of encapsulated beads, biodegradables or other materials situated within the protected regions or contained within the material of the entire stent.

The inventors have found that compositions deposited or otherwise situated or positioned in the protected regions or portions of the stents can be any composition provided that the composition is brought into proximity, preferable close proximity, or into contact, preferably direct contact, with a vessel's interior surface or tissue of a tissue site after stent deployment. The term proximity means sufficiently close to a desired site that the composition can impart the desired prophylactic and/or therapeutic effect to the site. The term close proximity means sufficiently close to the desired site that the composition can impart substantially the entire desired effect at or to the desired site.

The compositions can have substantially uniform, variable and/or differential permeability and/or porosity and/or height. The compositions can be permeable to bodily fluids in general or to constituents thereof. Moreover, the permeability can vary across a desired profile of the composition or throughout the entire composition, i.e., the composition have a permeability gradient across a desired profile of the composition. Additionally, the compositions can have porosities that also vary across a desired profile of the composition or throughout the entire composition, i.e., the composition have a porosity gradient across a desired profile of the composition. Composition permeability (or permeabilities to desired constituents of bodily fluids) can range from essentially or substantially impermeable to highly permeable to bodily fluids in general or to desired constituents of bodily fluids. That is, the compositions may have include gradients of pores (voids), material content, bioactive agents or the like. These gradients can change abruptly as in discontinuous changes in materials, smoothly so the property changes smoothly across a given profile of the composition or peaked where the permeability goes through maxima and minima across the profile.

Preferably, the compositions deposited in the protected zones of the stents of the present invention are encapsulated in an encapsulation matrix which is designed to rupture during stent deployment or bioerode after deployment. The encapsulated compositions can simply be bioactive agents designed to impart a desired prophylactic and/or therapeutic effect on the site where the stent is deployed. The encapsulated compositions can be bioactive agents dispersed in a bioerodible matrix that controls the release of the agents via bioerosion or degradation. The physical structures can also be encapsulated such as sharp crystals, crystalline structures, micro or nano structures, mechanical, electrical, electromechanical devices for penetrating into the interior surface of the vessel or into the tissue of a tissue site. Additionally, the crystals can be electrically or magnetically active so that the application of an oscillating external electric or magnetic field will cause the crystals to undergo alignment and dealingment with the lines of force inducing an abrading action similar to a motion of crystals in piezoelectric transducer. Moreover, the non-crystal structures can be magnetically or electrically active so that they will move in response to an applied external field, e.g., oscillate in response to an oscillating field, turn in response to an external field, or undergo so other motion in response to an applied external field. Mixtures or combinations of penetrating mechanical or physicals structure (bio or non-bio degradable) and bioactive agents (chemicals, pharmaceuticals, enzymes, genes, or other gene delivery systems such as retroviruses, adenoviruses, viral vectors, plasmids, liposomes containing DNA or RNA or the like) can also be encapsulated so that the mechanical or physical structures will perforate the tissue or the interior surface of the vessel (plaque or vessel wall) improving the availability of the bloactive agents.

The compositions of this invention may further contain other materials such as fillers to improve the strength of the materials such as polymer matrices, materials that will aid in degradation, anti-degradants such as anti-oxidants, biologically-active agents, colorants, chromophores or light activated (fluorescent orphosphorescent) tags or any other material that may alter or change the property of the compositions.

Another preferred form of the compositions and/or structures deposited in the protected regions or portions of the stents of the present invention is to coat the compositions and/or structures with a bioerodible coating. After bioerosion of the coating, the compositions and/or structures can impart their prophylactic and/or therapeutic effect to a vessel or tissue.

Bioactive Agent

Bioactive agents or biologically-active agents which may be used alone or in combination with bioerodible polymers include medicines, pharmaceuticals, drugs, or any suitable biologically-, physiologically- or pharmacologically-active substances which are capable of providing local biological or physiological activity to the interior surfaces of vessels or to tissues of an animal, including a human, and if contained in an erodible polymer or polymer matrix are capable of being released from the polymer matrix into interior or interior surface of vessels such as blood vessels, bile ducts, ureters, pancreatic ducts, etc. or into tissues.

If the biologically-active agent(s) are to be added to the polymer composition during preparation, then the agent(s) are not altered by the polymer, the solvent, if one is used or the preparation conditions. Generally, the agents are simply added to the polymer and the mixture is stirred to produce a homogeneous composition and if a solvent is used, the solvent is removed by any technique that does not result in the dilution, removal, degradation and/or decomposition of the bioactive agent.

Suitable biologically-active agents also include substances useful in preventing infection at the composition site, as for example, antiviral, antibacterial, antiparasitic, antifungal substances and combinations thereof. The agent may further be a substance capable of acting as a stimulant, sedative, hypnotic, analgesic, anticonvulsant, and the like. The compositions of this invention can contain large numbers of biologically-active agents either singly or in combination. Examples of these biologically-active agents include, but are not limited to: (1) anti-inflammatory agents such as hydrocortisone, prednisone, fludrotisone, triamcinolone, dexamethasone, betamethasone and the like; (2) antibacterial agents such as penicillins, cephalosporins, vancomycin, bacitracin, polymycins, tetracyclines, chloramphenicol, erythromycin, streptomycin, and the like; (3) antiparasitic agents such as quinacrine, chloroquine, quinine, and the like; (4) antifungal agents such as nystatin, gentamicin, miconazole, tolnaftate, undecyclic acid and its salts, and the like; (5) antiviral agents such as vidarabine, acyclovir, ribarivin, amantadine hydrochloride, iododeoxyuridine, dideoxyuridine, interferons and the like; (6) antineoplastic agents such as methotrexate, 5-fluorouracil, bleomycin, tumor necrosis factor, tumor specific antibodies conjugated to toxins, and the like; (7) analgesic agents such as salicylic acid, salicylate esters and salts, acetaminophen, ibuprofen, morphine, phenylbutazone, indomethacin, sulindac, tolmetin, zomepirac, and the like; (8) local anaesthetics such as cocaine, benzocaine, novocaine, lidocaine, and the like; (9) vaccines such as hepatitis, influenza, measles, mumps, rubella, hemophilus, diphtheria, tetanus, rabies, polio, and the like; (10) central nervous system agents such as tranquilizers, sedatives, anti-depressants, hypnotics, B-adrenergic blocking agents, dopamine, and the like; (11) growth factors such as colony stimulating factor, epidermal growth factor, erythropoietin, fibroblast growth factor, neural growth factor, human growth hormone, platelet derived growth factor, insulin-like growth factor, and the like; (12) growth factor inhibitors such as inhibitors for colony stimulating factor, epidermal growth factor, erythropoietin, fibroblast growth factor, neural growth factor, human growth hormone, platelet derived growth factor, insulin-like growth factor, and the like; (13) hormones such as progesterone, estrogen, testosterone, follicle stimulating hormone, chorionic gonadotrophin, insulin, endorphins, somatotropins and the like; (14) antihistamines such as diphenhydramine, chlorpheneramine, chlorcyclizine, promethazine, cimetidine, terfenadine, and the like; (15) cardiovascular agents such as verapamil hydrochloride, digitalis, streptokinase, nitroglycerine paparefine, disopyramide phosphate, isosorbide dinitrate, and the like; (16) bronchodilators such as metaprot-ernal sulfate, aminophylline, albuterol, and the like; and/or (17) vasodilators such as theophylline, niacin, nicotinate esters, amylnitrate, minoxidil, diazoxide, nifedipine, and the like.

As the compositions biodegrades and/or bioerodes, the biologically-active agent may be released from the matrix into the adjacent tissue fluids. The biologically-active agent can be released into the surrounding tissue or bodily fluids at a controlled rate (a biodegradation of a uniform matrix), intermittently (layers of agents and biodegradables), or a delayed time. For example, the polymer matrix may be formulated to degrade after an effective and/or substantial amount of the biologically-active agent is released from the matrix. Release of a biologically-active agent having a low solubility in water, as for example a peptide or protein, may require the degradation of greater amounts of the polymer matrix to expose the agent directly to the surrounding tissue fluids. Thus, the release of the biologically-active agent from the matrix may be varied by, for example, the solubility of the biologically-active agent in water, the distribution of the biologically-active agent within the matrix, or the size, shape, porosity, solubility and biodegradability of the polymer matrix, among other factors.

The biologically-active agent may also be a substance or metabolic precursor thereof, which is capable of promoting growth and survival of cells and tissues, or augmenting the activity of functioning cells, as for example, blood cells, neurons, muscle, bone marrow, bone cells and tissues, and the like, especially endothelial cells in the case of vessels in the body. For example, the biologically-active agent may be a nerve growth promoting substance, as for example, a ganglioside, phosphatidylserine, a nerve growth factor, brain-derived neurotrophic factor, a fibroblast growth factor, and the like.

To promote tissue growth, the biologically-active agent may be either a hard or soft tissue promoting substance or combinations thereof. Suitable peptides and/or tissue growth promoting agents include, for example, fibronectin (FN), endothelial cell growth factor (ECGF), cementum attachment extracts (CAE), human growth hormone (HGH), a Periodontal ligament cell growth factor, fibroblast growth factor (FGF), animal growth hormones, platelet derived growth factor (PDGF), epidermal growth factor (EGF), protein growth factor interleukin-1 (IL-1), transforming growth factor (TGF beta-2), insulin-like growth factor II (ILGF-II), human alpha thrombin (HAT), osteoinductive factor (OIF), bone morphogenetic protein (BMP) or protein derived therefrom, demineralized bone matrix, and releasing factors thereof.

The biologically-active agent may also be a substance or metabolic precursor thereof, which is capable of inhibiting or retarding growth and/or cell survival or augmenting the activity of functioning cells, especially endothelial cells. The inhibiting biologically-active agents may be either a hard or soft tissue inhibiting substance or combinations thereof. Suitable agents include agents that can interfere with or inhibit the action of fibronectin (FN), endothelial cell growth factor (ECGF), cementum attachment extracts (CAE), human growth hormone (HGH), a Periodontal ligament cell growth factor, fibroblast growth factor (FGF), animal growth hormones, platelet derived growth factor (PDGF), epidermal growth factor (EGF), protein growth factor interleukin-1 (IL-1), transforming growth factor (TGF beta-2), insulin-like growth factor II (ILGF-II), human alpha thrombin (HAT), osteoinductive factor (OIF), bone morphogenetic protein (BMP) or protein derived therefrom, demineralized bone matrix, and releasing factors thereof.

Other suitable bioactive agents include, without limitation, DNA, RNA, or DNA/RNA sequences that encode for proteins involved in NO regulator proteins and/or enzymes, VEFT or any of the other above-identified proteins, enzymes or the like. Additionally, the genetic material may include up regulator factors or suppressor factors for changing or augmenting the normal production of certain proteins, enzymes or the like.

Encapsulating Bioactive Agents

Suitable encapsulating agents include, without limitation, any encapsulating formation approved for use in the body including all of the biodegradable polymers mentioned previously in connection with bioactive agents. Moreover, photopolymerizable monomers capable of being polymerized in situ and to cover the recessed areas. Deployment would then result in the rupturing of the covering. Additionally, starch and sugar based material can be used as an encapsulating covering over the composition and/or structures in the protected zones of the stents of the present invention.

Bioerodible Polymers and Polymeric Compositions

Suitable polymers for use in the present invention include, without limitation, biocompatible polymers, preferably biocompatible polymers that are biodegradable and/or bioerodible, i.e., the polymers eventually decompose in the body. The biodegradation and/or bioerodible can be by cellular degradation (e.g., macrophage degradation or the like), chemical degradation (e.g., enzymatic degradation), hydrolysis (e.g., via bodily fluids such as plasma) or other cellular action and/or the degradation or erosion can be due to degradation agents contained within the composition itself (e.g., embedded enzymes, depolymerization agents or the like). Such polymeric substances include polyesters, polyamides, polypeptides and/or polysaccharides or the like.

Non-limiting examples of suitable biocompatible, biodegradable polymers, include polylactides, polyglycolides, polyfumarates, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or higher polymonomer polymers thereof or combinations or mixtures thereof. The preferred biodegradable polymers are all degraded by hydrolysis.

Typically, the polymers will either be surface erodible polymers such as polyanhydrides or bulk erodible polymers such as polyorthoesters. Poly(l-lactic acid) (PlLA), poly(dl-lactic acid) (PLA), poly(glycolic acid) (PGA), polycaprolactones, copolymers, terpolymer, higher poly-monomer polymers thereof, or combinations or mixtures thereof are preferred biocompatible, biodegradable polymers. The preferred biodegradable copolymers are lactic acid and glycolic acid copolymers sometimes referred to as poly(dl-lactic-coglycolic acid) (PLG). The co-monomer (lactide:glycolide) ratios of the poly(DL-lactic-co-glycolic acid) are preferably between about 100:0 to about 50:50 lactic acid to glycolic acid. Most preferably, the co-monomer ratios are between about 85:15 and about 50:50 lactic acid to glycolic acid. Blends of PLA with PLG, preferably about 85:15 to about 50:50 PLG to PLA, are also used to prepare polymer materials.

PLA, PlLA, PGA, PLG and combinations or mixtures or blends thereof are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid.

To enhance bio-degradation of the polymers used in biological application, the compositions of the present invention can also include the addition of enzymes that can facilitate the biodegradation of the polymers used in the composition. Preferred enzymes or similar reagents are proteases or hydrolases with ester-hydrolyzing capabilities. Such enzymes include, without limitation, proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, an oxidoreductase, an oxidase or the like. The inclusion of an appropriate amount of such a degradation enhancing agent can be used to regulate composition duration.

Suitable Solvents for Use in Forming the Bioactive Compositions

Suitable polymers can be combined with suitable organic solvents to form polymeric solutions. The solubility or miscibility of a polymer in a particular solvent will vary according to factors such as crystallinity, hydrophilicity, capacity for hydrogen-bonding and molecular weight of the polymer. Consequently, the molecular weight and the concentration of the polymer in the solvent are adjusted to achieve the desired miscibility and/or viscosity. Preferred polymers are those which have a low degree of crystallinity a low degree of hydrogen-bonding, low solubility in water, and high solubility in organic solvents.

In general, the polymers are dissolved in a suitable organic solvent. The solvent should not adversely affect the polymer or the particulate solids and preferably should be a volatile organic solvent. The relative amount of solvent will have a minimal effect on the structure of the produced materials, but will affect the solvent evaporation time.

Solvents which may be used to make polymeric compositions of the invention include, without limitation, N-methyl-2-pyrrolidone, 2-pyrrolidone, C2 to C6 alkanols, propylene glycol, acetone, alkyl esters such as methyl acetate, ethyl acetate, ethyl lactate, alkyl ketones such as methyl ethyl ketone, dialkylamides such as dimethylformamide, dimethyl sulfoxide, dimethyl sulfone, tetrahydrofuran, cyclic alkyl amides such as caprolactam, decylmethylsulfoxide, oleic acid, propylene carbonate, aromatic amides such as N,N-diethyl-m-toluamide, and 1-dodecylazacycloheptan-2-one. Preferred solvents according to the invention include N-methyl-2-pyrrolidone, 2-pyrrolidone, dimethyl sulfoxide, acetone, and propylene carbonate. Preferred solvents are simple ketones such as acetone, chlorinated hydrocarbons such as methylene chloride, chloroform, methylethylketone, or the like.

Preferred Stent Materials

Suitable materials that can be used to make the stents of the present invention include, without limitation, iron alloys such as stainless steels, titanium alloys, cobalt chrome alloys, nitinol, platinum-based alloys, gold and gold alloys, silver and silver alloys, polyolefins such as polyethylene, polypropylene, or the like, polyanhydride, polyorthoesters, polyurethane, polyesterurethane, polycaprolactone, polyacetal, polyethylene terephthalate or other polyesters, silicone, siloxanes, polysiloxanes, silicone rubbers, or other like silicone polymers, polylactides/polyglycolides, nylon or other polyamides, polycarbonate, fluorinated polyolefins such as Teflon®, acrylics such as polymethylmethacrylate, hyaluronic acid, collagens, hydroxyapatite, acellular tissue products, keratan, chitosan, other similar materials or mixtures or combinations thereof. For bioerodible stent, any of the bioerodible materials previously mentioned above can be used. Of course, the exact material should biodegrade at a rate slower to substantially slower than the rate of delivery of bioactive agents and/or structures.

Moreover, the stents may be a mixture of combination of material. Thus, the recessed regions may be polymeric, while the non-recessed regions may be metal; the recessed regions may be composed of a flexible or deformable polymer, while the non-recessed regions may be composed of a non-flexible or non-deformable polymer.

Preferred Materials for Use in the Compositions

The compositions to be situated inside the protected zones of the stents of the present invention are generally any bio-active agent, polymer matrix containing a bio-active agent or an encapsulated bio-active agent or a polymer matrix containing a bio-active agent or mixtures and combinations thereof designed to achieve a given therapeutic and/or prophylactic effect at the site of deployment. The stents can include a single bio-active agent or any number of bio-active agents and compositions to regulate the release of these bio-active agents.

Preferred Materials for Use in the Structures

The structures to be situated inside the protected zones of the stents of the present invention are generally any structure designed to achieve a given therapeutic and/or prophylactic effect at the site of deployment. The structures can simply be crystals or other relatively hard compounds or a mechanical, electrical, electromechanical device and may be porous ro hold the bioactive agents in large quantities. The crystals, compounds, or devices are generally small and typically range from about 1 nm in height to about 1 mm in height, preferably, from about 5 nm to about 500 μm in height and particularly, from about 50 nm to about 200 μm in height. The devices, compounds or crystals can also include bioactive agents that are delivered to the site of deployment concurrently with the action of the structures or at some time controlled by the structure itself, e.g., rate of degradation of the structures, controlled opening of a cavity, or a composition associated with the structures, where the composition is as set forth above. Additionally structures which can be used in the stents of this invention include the structure set forth in U.S. patent application Ser. No. 6,197,013, incorporated herein by reference.

Preferred Embodiments of the Stents Including Bioactive Agents

Referring now to FIGS. 1A–B, a first embodiment of a stent 100 of the present invention is shown in cross-section to have a generally triangular cross-section in its un-deployed state and a generally circular cross-section in its deployed state, respectively. The stent 100 includes three convex arcuate, non-recessed regions 102 and three concave recessed regions 104, where the regions 102 and 104 regions alternate. The stent 100 also includes a bioactive composition 106 deposited in protected zones 108 located in the recessed regions 104, where the composition 106 outer surface 107 is below an outer surface 103 of the non-recessed areas 102. The stent's cross-sectional dimension in its undeployed state, as shown in FIG. 1A, can be inscribed in a first circle 110 having a first diameter $d_1$ and after deployed, the stent assumes a substantially circular contour having a diameter $d_2$, where $d_2$ is greater than or equal to $d_1$.

Figure 1C:
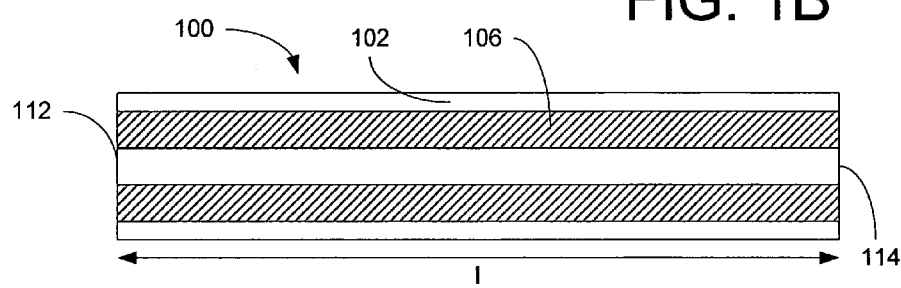
FIG. 1C is a side view of the stent of FIG. 1A in its deployed state.

Referring now to FIG. 1C, the stent 100 is shown in a side view where the non-recessed regions 102, the recessed regions 104 and the composition 106 contained therein run parallel down a length l of the stent 100 from a first end 112 to a second end 114.

Figures 1D, 1E:
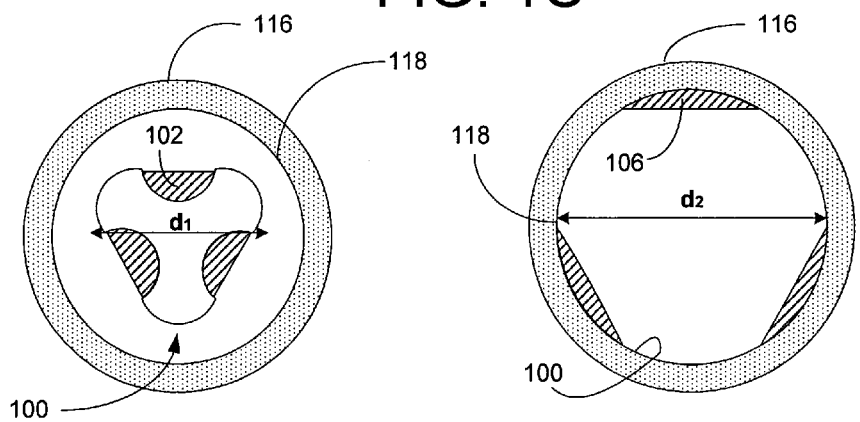
FIG. 1D is a radial cross-sectional view the stent of FIG. 1A in its undeployed state positioned within a blood vessel.
FIG. 1E is a radial cross-sectional view the stent of FIG. 1A in its deployed state now engaging an interior of the blood vessel.

Referring now to FIGS. 1D and E, the stent 100 is shown in its undeployed and its deployed states, respectively, positioned within a vessel 116 having an interior surface or lumen 118. After deployment of the stent 100 via radial expansion, the stent assumes a substantially circular cross-section having the diameter $d_2$, where $d_2$ is greater than or equal to $d_1$. As shown in FIG. 1E, the recessed regions 104 are extended and the protected zones 108 and the compositions 106 are elongated relative to their undeployed state bringing the composition 106 into contact with or proximity to the vessel's interior surface 118 or increasing the exposure of the vessel to the composition 106 originally contained within the protected zones 108.

Figure 2A:
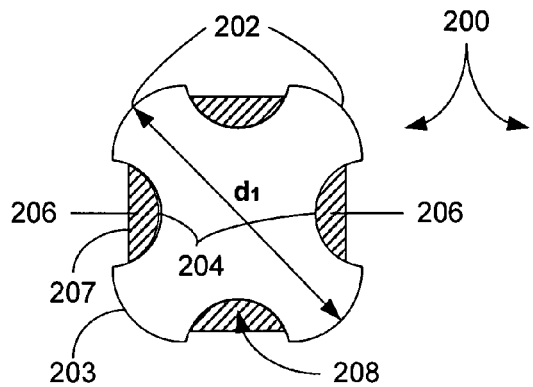
FIG. 2A is a radial cross-sectional view of a second preferred embodiment of a stent of the present invention in its undeployed state.
Figure 2B:
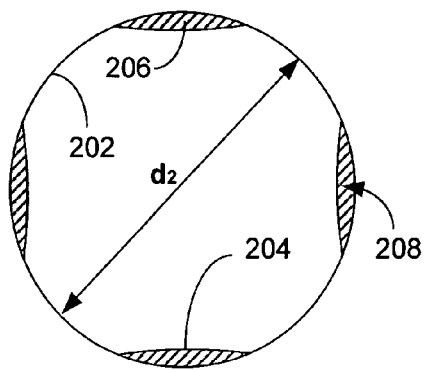
FIG. 2B is a radial cross-sectional view of the stent of FIG. 2A in its deployed state.

Referring now to FIGS. 2A–B, a second embodiment of a stent 200 of the present invention is shown in cross-section to have a generally square cross-section in its un-deployed state and a generally circular cross-section in its deployed state, respectively. The stent 200 includes four substantially rigid arcuate non-recessed regions 202 and four deformable, concave recessed regions 204 interposed between each pair of non-recessed regions 202 so that the regions 202 and 204 alternate. The stent 200 also includes a bioactive composition 206 deposited in protective zones 208 associated with each recessed region 204. Again, the composition 206 has an outer surface 207 that is below an outer surface 203 of the non-recessed areas 202.

In its undeployed state, the stent 200, as shown in FIG. 2A, has a first diameter or cross-sectional dimension of $d_1$ and after deployed, the stent 200 assumes a substantially circular contour having a diameter $d_2$ in its deployed state, where $d_2$ is greater than or equal to $d_1$.

Figure 2C:
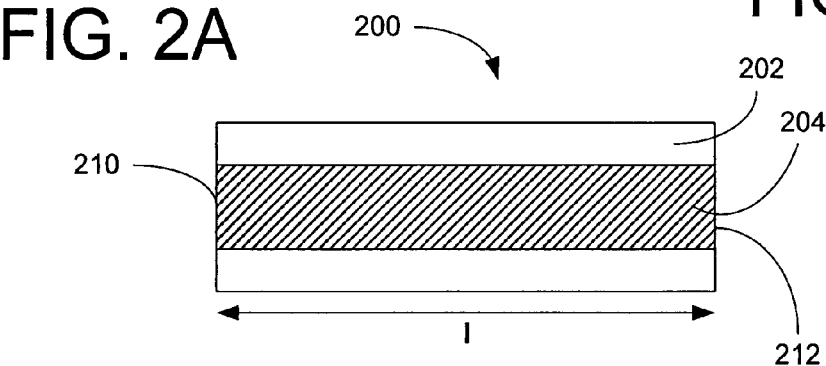
FIG. 2C is a side view of the stent of FIG. 2A in its deployed state.

Referring now to FIG. 2C, the stent 200 is shown in side view where the non-recessed region 202, the recessed regions 204 and the composition 206 contained therein run parallel down a length l of the stent 200 from a first end 210 to a second end 212.

Figure 2D:
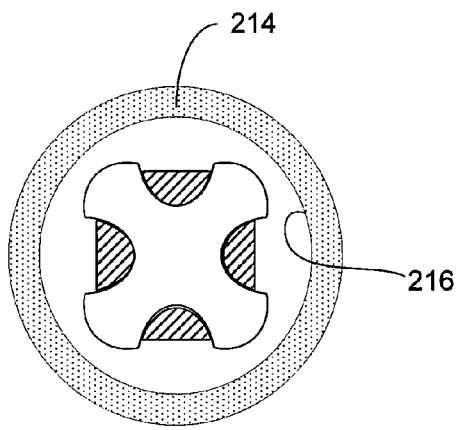
FIG. 2D is a radial cross-sectional view the stent of FIG. 2A in its undeployed state positioned within a blood vessel.
Figure 2E:
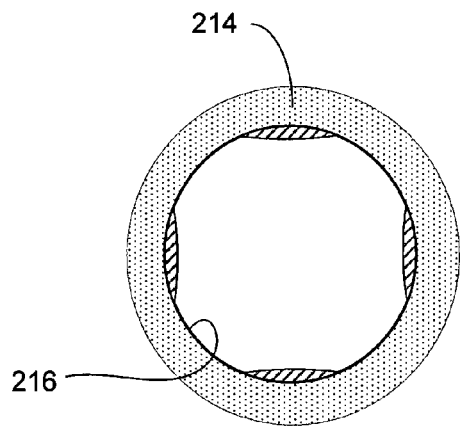
FIG. 2E is a radial cross-sectional view the stent of FIG. 2A in its deployed state now engaging an interior of the blood vessel.

Referring now to FIGS. 2D–E, the stent 200 is shown in its undeployed and its deployed state within a vessel 214 having an interior surface or lumen 216. After deployment of the stent 200 via primarily radial expansion, a stent's cross-sectional dimension is now $d_2$, which is greater than or equal to $d_1$, bringing the composition 206 in the elongated and flattened recessed regions 204 into contact with or proximity to the interior surface 216 of the vessel 214 or exposes a greater amount of the interior surface 216 to the composition 206.

Figures 3A, 3B:
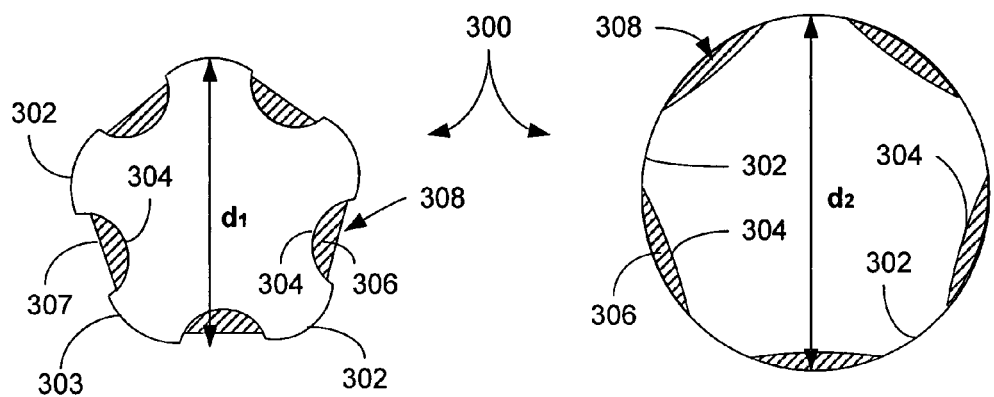
FIG. 3A is a radial cross-sectional view of a third preferred embodiment of a stent of the present invention in its undeployed state.
FIG. 3B is a radial cross-sectional view of the stent of FIG. 3A in its deployed state.

Referring now to FIGS. 3A–B, a third embodiment of a stent 300 of the present invention is shown in cross-section to have a generally pentagonal (5-sided) cross-section in its un-deployed state and a generally circular cross-section in its deployed state, respectively. The stent 300 includes five substantially rigid arcuate non-recessed regions 302 and five deformable, recessed regions 304 interposed between each pair of non-recessed regions 302 so that the regions 302 and 304 alternate. The stent 300 also includes a bioactive composition 306 deposited in protected zones 308 associated with each recessed region 304. Again, the composition 306 has an outer surface 307 that is below an outer surface 303 of the non-recessed areas 302. The stent 300 has an undeployed or first diameter or cross-sectional dimension (largest cross-sectional dimension) $d_1$ and a deployed or second diameter or cross-sectional dimension (largest cross-sectional dimension) $d_2$, where $d_2$ is greater than or equal to $d_1$.

Figure 3C:
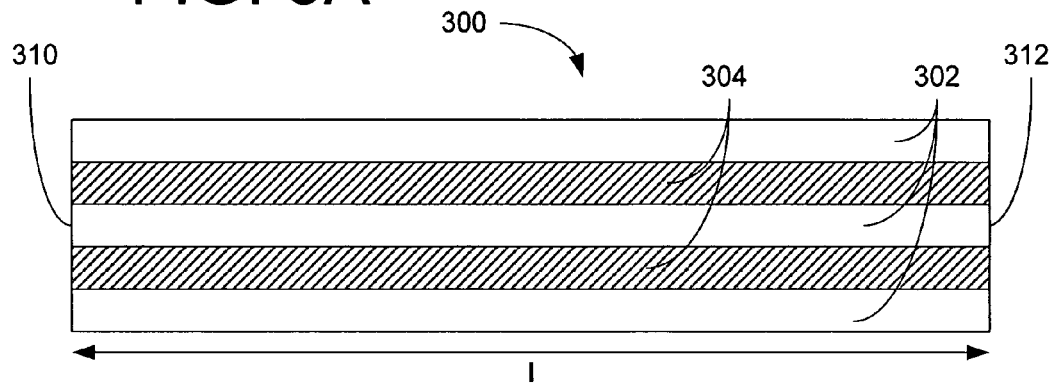
FIG. 3C is a side view of the stent of FIG. 3A in its deployed state.

Referring now to FIG. 3C, the stent 300 is shown in a side view where the non-recessed region 302, the recessed regions 304 and the composition 306 contained therein run parallel down a length l of the stent 300 from a first end 310 to a second end 312.

Figures 3D, 3E:
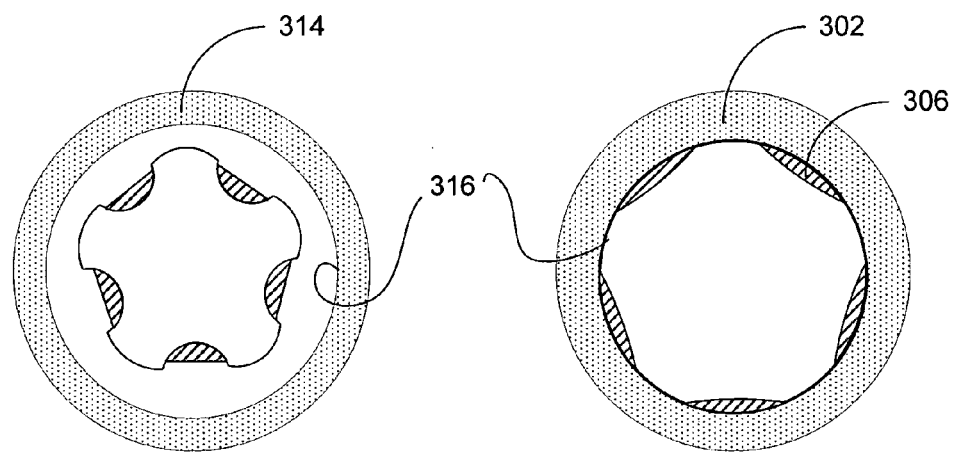
FIG. 3D is a radial cross-sectional view the stent of FIG. 3A in its undeployed state positioned within a blood vessel.
FIG. 3E is a radial cross-sectional view the stent of FIG. 3A in its deployed state now engaging an interior of the blood vessel.

Referring now to FIGS. 3D–E, the stent 300 is shown in its undeployed and its deployed state within a vessel 314 having an interior surface or lumen 316, respectively. After deployment of the stent 300 via primarily radial expansion, the stent's cross-sectional dimension is now $d_2$, which is greater than $d_1$, bringing the composition 306 in the elongated and flattened recessed regions 304 into contact with or proximity to the interior surface 316 of the vessel 314 or exposes a greater amount of the interior surface 316 to the composition 306.

Figures 4A, 4B:
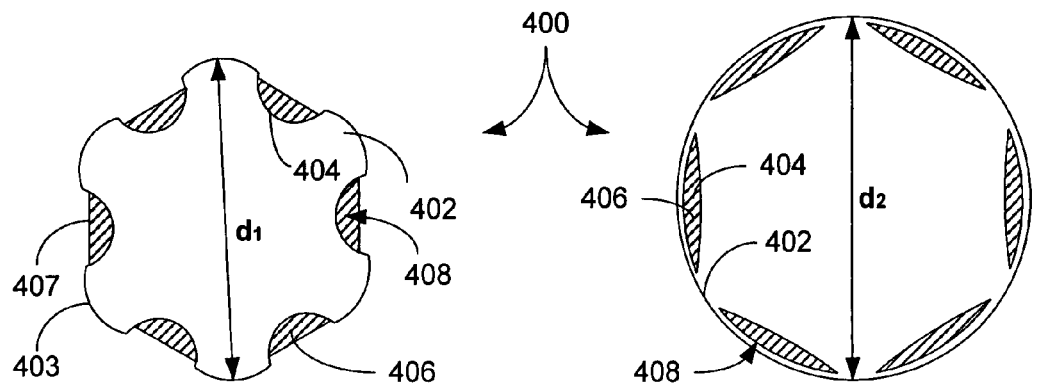
FIG. 4A is a radial cross-sectional view of a fourth preferred embodiment of a stent of the present invention in its undeployed state.
FIG. 4B is a radial cross-sectional view of the stent of FIG. 4A in its deployed state.

Referring now to FIGS. 4A–B, a fourth embodiment of a stent 400 of the present invention is shown in cross-section to have a generally hexagonal (6-sided) cross-section in its un-deployed state and a generally circular cross-section in its deployed state, respectively. The stent 400 includes six substantially rigid arcuate non-recessed regions 402 and six deformable, recessed regions 404 interposed between each pair of non-recessed regions 402 so that the regions 402 and 404 alternate. The stent 400 also includes a bioactive composition 406 deposited in protective zones 408 associated with each recessed region 404. Again, the composition 406 has an outer surface 407 that is below an outer surface 403 of the non-recessed areas 402.

The stent 400 has an undeployed or first diameter or cross-sectional dimension (largest cross-sectional dimension) $d_1$ and a deployed or second diameter or cross-sectional dimension (largest cross-sectional dimension) $d_2$ where $d_2$ is greater than or equal to $d_1$. In this embodiment, the compositions 406 deposited in the zones 408 remain recessed below the non-recessed regions 402, i.e., the outer surface 407 of the compositions 406 are below the outer surface 403 of the non-recessed regions 402 even after deployment.

Figure 4C:
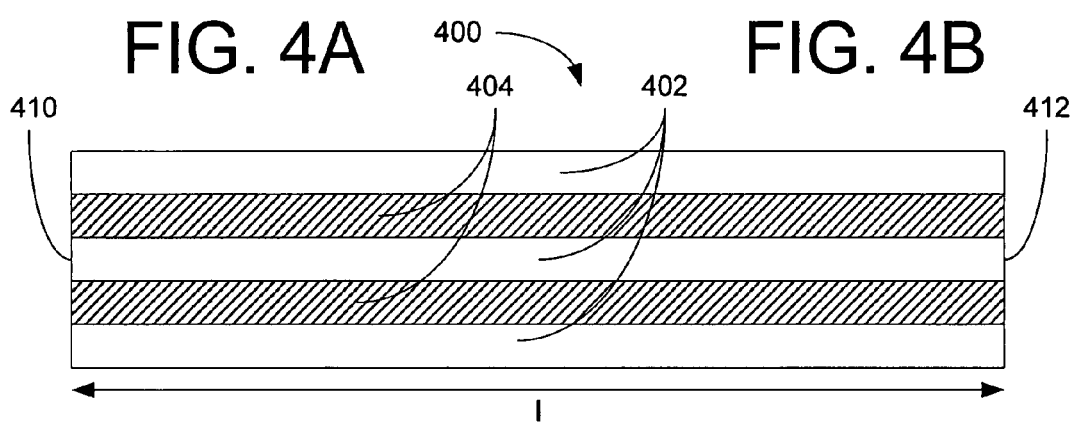
FIG. 4C is a side view of the stent of FIG. 4A in its deployed state.

Referring now to FIG. 4C, the stent 400 is shown in a side view where the non-recessed region 402, the recessed regions 404 and the composition 406 contained therein run parallel down a length l of the stent 400 from a first end 410 and a second end 412.

Figures 4D, 4E:
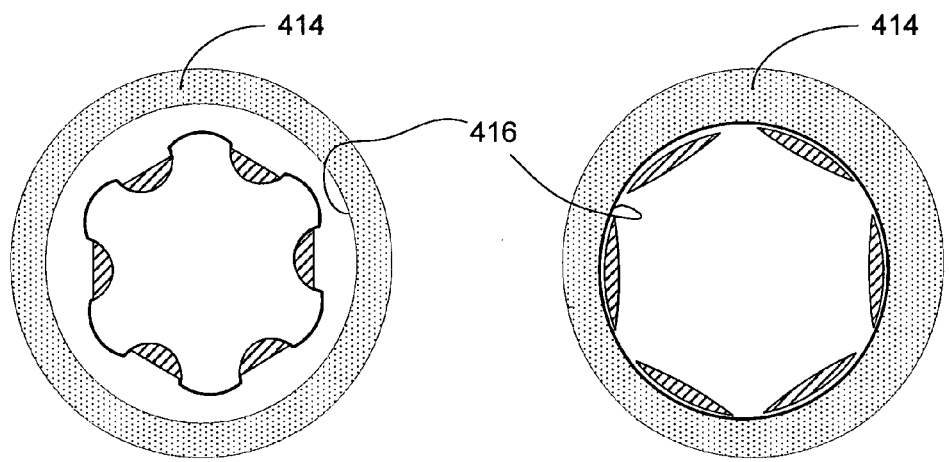
FIG. 4D is a radial cross-sectional view the stent of FIG. 4A in its undeployed state positioned within a blood vessel.
FIG. 4E is a radial cross-sectional view the stent of FIG. 4A in its deployed state now engaging an interior of the blood vessel.

Referring now to FIGS. 4D–E, the stent 400 is shown in its undeployed and its deployed state within a vessel 414 having an interior surface or lumen 416. After deployment of the stent 400 via primarily radial expansion, the stent's cross-sectional dimension is now $d_2$, which is greater than $d_1$, bringing the composition 406 in the elongated and flattened recessed regions 404 into contact with or proximity to the interior surface 416 of the vessel 414 or exposes a greater amount of the interior surface 416 to the composition 406.

Figure 5A:
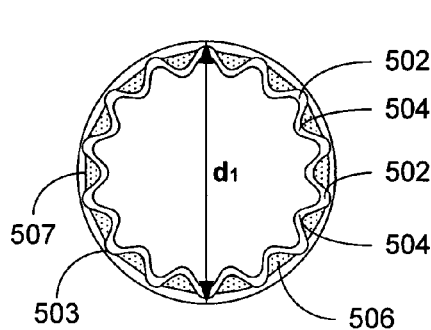
FIG. 5A is a radial cross-sectional view of a fifth preferred embodiment of a stent of the present invention in its undeployed state.
Figure 5B:
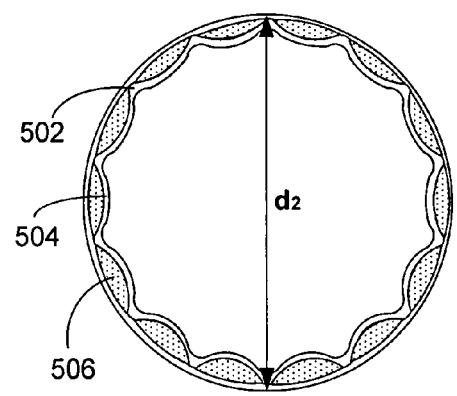
FIG. 5B is a radial cross-sectional view of the stent of FIG. 5A in its deployed state.

Referring now to FIGS. 5A–B, a fifth embodiment of a stent 500 of the present invention is shown in cross-section to have a generally pleated cross-section in its un-deployed state and a generally circular cross-section in its deployed state, respectively. The stent 500 includes alternating peaks or pleats 502 and deformable recessed regions 504. The stent 500 also includes a bioactive composition 506 deposited in protected zones 504 within the recessed regions 504. Again, the composition 506 has an outer surface 507 that is below an outer surface 503 of the non-recessed areas 502. The stent 500 has an undeployed or first diameter or cross-sectional dimension (largest cross-sectional dimension) $d_1$ and a deployed or second diameter or cross-sectional dimension (largest cross-sectional dimension) $d_2$, where $d_2 \geq d_1$.

Figure 5C:
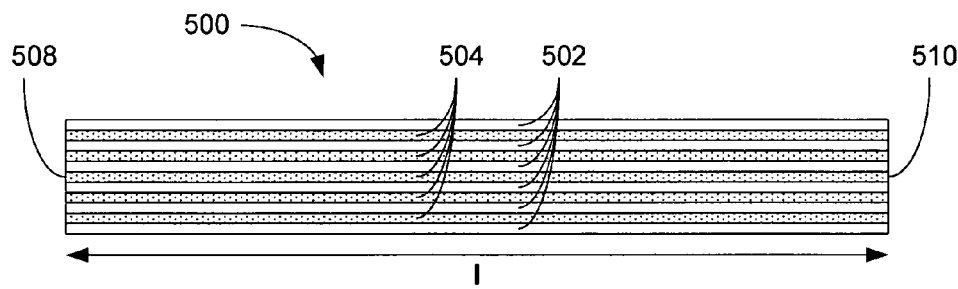
FIG. 5C is a side view of the stent of FIG. 5A where the stent is not twisted axially.

Referring now to FIG. 5C, the stent 500 is shown in a side view where the peaks (non-recessed regions) 502, the valleys (non-recessed regions) 504 and the composition 506 contained therein run parallel down a length l of the stent 500 from a first end 508 and a second end 510.

Figure 5D:
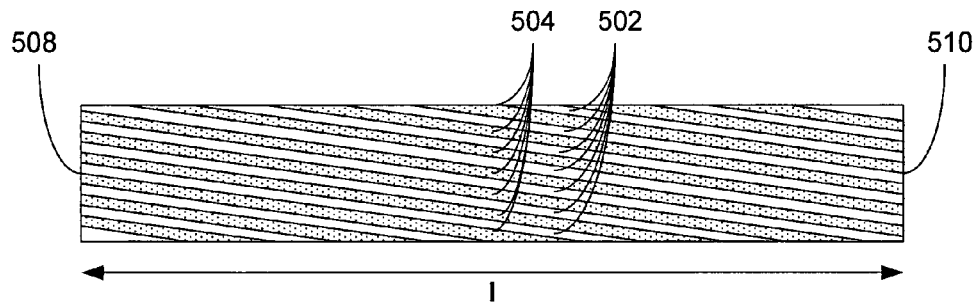
FIG. 5D is a side view of the stent of FIG. 5A where the stent is twisted axially into a helical configuration.

Alternatively, referring now to FIG. 5D, the peaks 502, the valleys 504 and the composition 506 contained therein of the stent 500 are arranged in a helical structure down the length l of the stent 500 from the first end 508 and the second end 510 where the helix has a twist angle of θ, where θ can range from about 0° (no twist or parallel orientation) to as high as is commercially practicable, but generally not exceeding about 120°. It should be recognized that all of the stents described in the preferred embodiments and illustrated by the FIGS. 1A–4E can have helically oriented recessed and non-recessed regions and that the number of alternating recessed and non-recessed regions is limited only by manufacturing criteria depending on the nature of the stent material.

As with the other preferred embodiments described above, after deployment, the pleated stent 500 via primarily radial expansion, assumes a cross-sectional dimension $d_2$ bringing the composition into contact with or proximity to an interior surface of a vessel (not shown) or exposes a greater amount of the interior surface to the composition.

Referring now to FIGS. 6A–E, a sixth embodiment of a stent 600 of the present invention is shown in cross-section to have a generally circular cross-sectional contour in its un-deployed state and in its deployed state, respectively. The stent 600 includes a substantially rigid outer surface 602 and an inner surface 604. Interposed between the outer surface 602 and the inner surface 604 is a bioactive composition 606. The composition 606 extends from a first surface 608 to a second surface 610 which is below the outer surface 602. The outer surface 602 has a diameter of $d_1$ which corresponds to the o.d. of the stent 600 in its undeployed state and the inner surface 604 has a diameter of $d_2$ which corresponds to the i.d. of the stent 600 in its undeployed state.

Figure 6A:
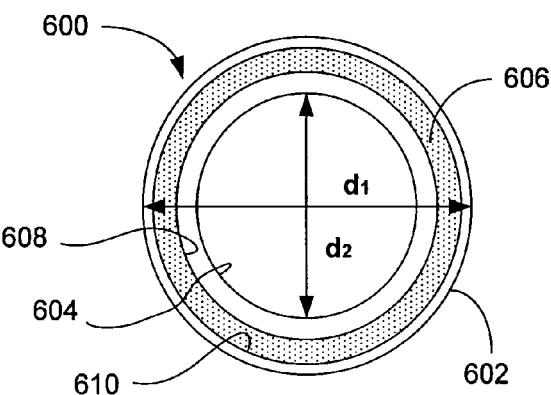
FIG. 6A is a radial cross-sectional view of a sixth preferred embodiment of a stent of the present invention in its undeployed state.
Figure 6B:
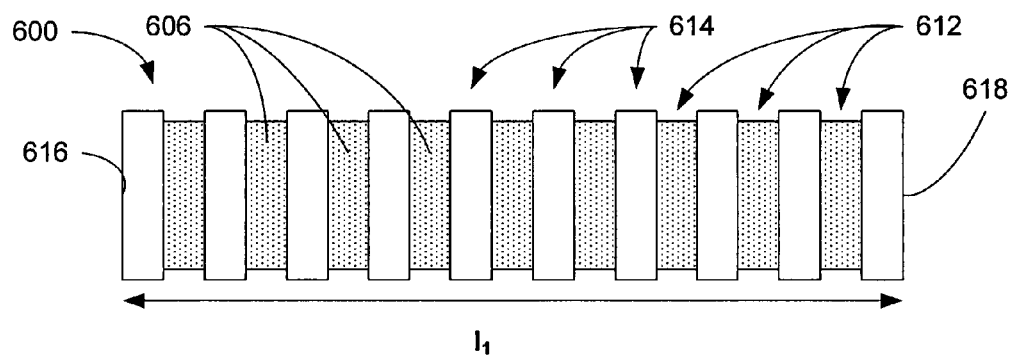
FIG. 6B is a side view of the stent of FIG. 6A in its undeployed state.
Figure 6C:
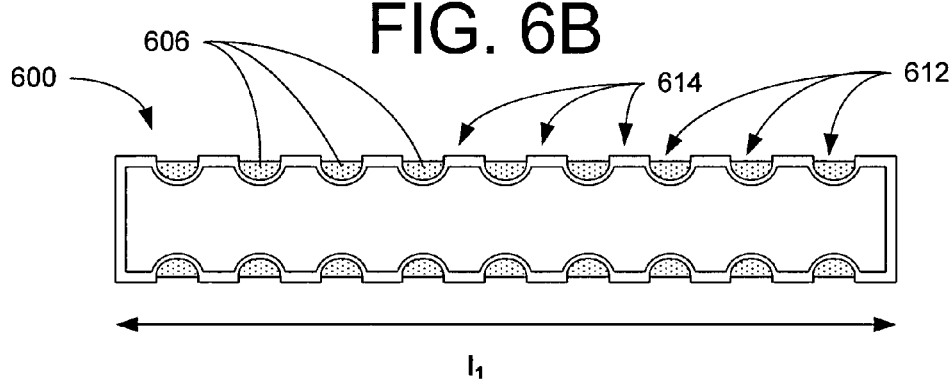
FIG. 6C is an axial cross-sectional view the stent of FIG. 6A in its undeployed state.

Referring now to FIGS. 6B and C, when applied between the inner surface 604 and the outer surface 602, the composition 606 appears as a series of alternating bands 612 and raised bands 614 circumscribing the stent 600 along an undeployed length $l_1$ from a first end 616 to a second end 618.

Figure 6D:
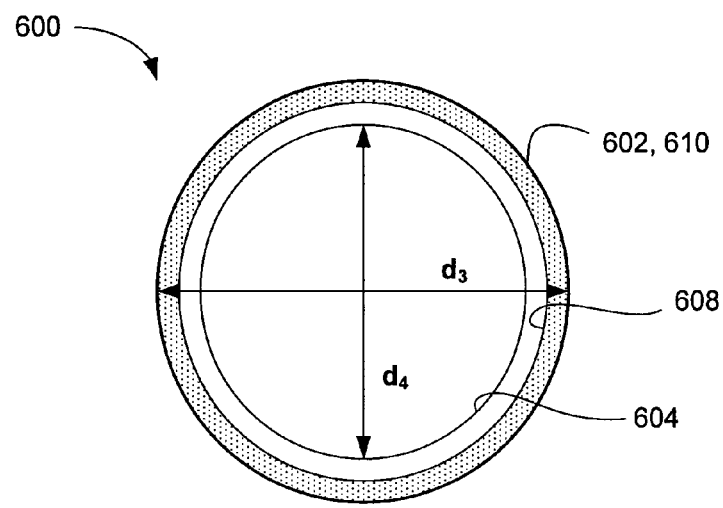
FIG. 6D is a radial cross-sectional view of the stent of FIG. 6A in its deployed state.
Figure 6E:
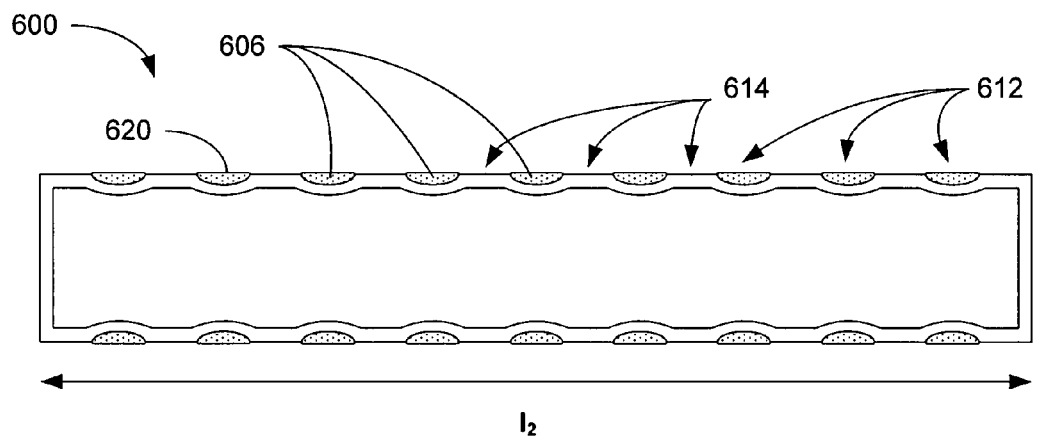
FIG. 6E is an axial cross-sectional view the stent of FIG. 6A in its deployed state.

Referring now to FIGS. 6D and E, the stent 600 is shown after deployment where the surfaces 602 and 610 have a diameter $d_3$ corresponding to the o.d. of the stent 600 in its deployed state and which is greater than or equal to the diameter $d_1$. The inner surface 604 has a diameter of $d_4$ after stent deployment corresponding to the i.d. of the stent 600 in its deployed state and is greater than or equal to the diameter $d_2$. In addition to radial expansion, the stent 600 undergoes longitudinal or axial expansion. Thus, after deployment the length $l_2$ of the stent 600 increase (see FIG. 6E). However, the stent 600 can be designed so that $l_2$ is substantially equal to $l_1$. Moreover, after deployment the compositional bands 612 elongate and expand so that their outer surface 620 is brought into contact with or proximity to the interior of a vessel's interior surface or with a tissue.

Figure 7A:
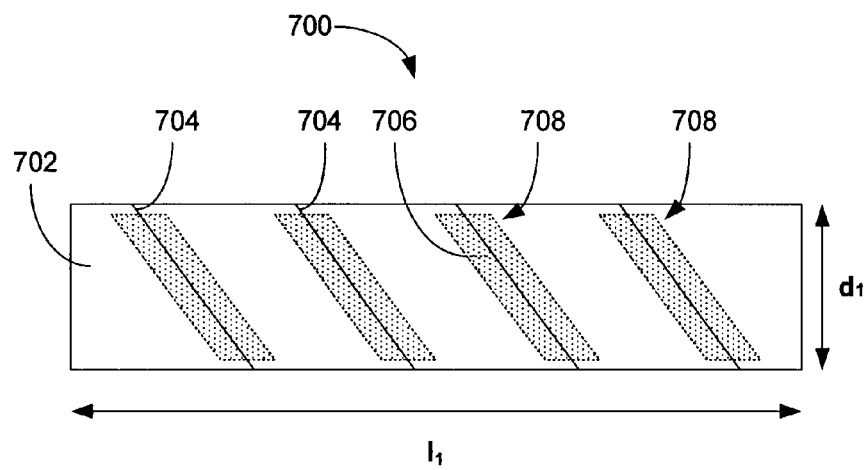
FIG. 7A is a side view of a seventh preferred embodiment of a stent of the present invention in its non-deployed state.

Referring now to FIG. 7A, a seventh embodiment of a stent of the present invention generally 700 is shown in a side view. The stent 700 is of a hollow, substantially cylindrical shape having a length $l_1$ and a diameter $d_1$. In its undeployed state, the stent 700 is designed to close outer regions 702 along seams 704 which seal and protect a bioactive composition 706 with recessed regions 708 of the stent 700.

Figure 7B:
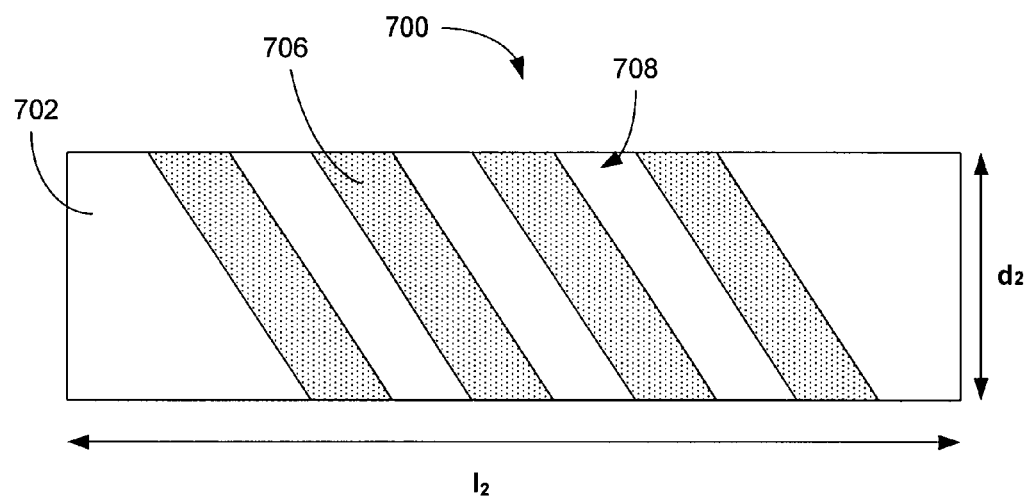
FIG. 7B is a side view of the stent of FIG. 7A in its undeployed state.

Referring now to FIG. 7B, the stent 700 is shown after deployment as a hollow, generally cylinder shape having a length $l_2$ and a diameter $d_2$, where $l_2 \geq l_1$ and $d_2 \geq d_1$. In its undeployed state, the stent 700 is designed to expand radially and longitudinally raising and exposing the recessed regions 708 thereby bringing the bioactive composition 706 into contact with or proximity to a tissue or an interior of a vessel.

Referring now to FIGS. 8A–B, an eighth embodiment of a stent of the present invention 800 is shown in a cross-section in its undeployed state (FIG. 8A) and in its deployed state (FIG. 8B). The stent 800 comprises a hollow, substantially cylindrical shape having an undeployed diameter $d_1$ and a deployed diameter $d_2$, where $d_2 \geq d_1$. The stent 800 includes covering regions 802 that close along seams 804 which seal and protect a bioactive composition 806 contained within covered regions 808 of the stent 800.

In its undeployed state, the stent 800 is under tension, either compressive tension and/or expansive tension, so that the covering regions 802 close at seams 804 to cover and protect the composition 806 contained within the covered regions 808.

Referring now to FIGS. 8C–D, the stent 800 is shown before and after deployment as a hollow, generally cylinder shape having an undeployed length $l_1$ and a deployed length $l_2$, where where $l_2 > l_2$. In its undeployed state, the stent 800 is designed to expand radially and longitudinally raising and exposing the covered regions 808 thereby bringing the bioactive composition 806 into contact with or proximity to a tissue or an interior of a vessel.

Although the embodiments depicted in FIGS. 7A to 8D show the covering regions close completely, alternate constructions include constructions where the stents are compressed so that in the undeployed state less composition is exposed than in the deployed state. That is, when the stent is tension to its undeployed state, the covering regions do not come into contact, but are simply brought closer together than in their deployed state.

Although this embodiments depicted in this section are shown either with final circular cross-sections or starting an final circular cross-sections, the stents can be constructed so that the initial and/or final cross-sectional contour is any contour that can be constructed or manufactured or that satisfies the design criteria for deployment in a given site in a body. Thus, the stents can have initial or final cross-sections that are oval, polygonal (trigonal, quadrilateral, pentagonal, etc.), pleated, banded, irregular or mixtures or combinations thereof.

If the compositions protected in the protected zones of any of the stents described in the figures above comprises a composition encapsulated by a encapsulating material, then elongation will generally result in a rupture of the encapsulating material. Alternatively, if the composition comprises small beads or capsules surrounded by encapsulating material, then elongation will generally result in the rupture of some or all of the capsules. Alternatively, the encapsulating material may be designed to degrade in a biological setting after some specific time after deployment. Of course, the capsules can be designed to have different degradation rates so that the delivery of bioactive agents is extended over a given period of time. Although this embodiment described in the figures above include a composition contained in the protected zones, it should be recognized that penetrating structures can also be used in addition to or in conjunction with the compositions. In fact, the penetrating structures and compositions can be constructed so that deployment brings the tissue site into contact first with the penetrating structure and/or compositions. These structures would open the tissue site so that the bioactive agents would have improved bio-availability to a targeted site.

Preferred Embodiments of the Stents Including Penetrating Structures

Referring now to FIGS. 9A–B, an illustrative embodiment of a stent of the present invention 900 is shown in cross-section to have a generally hexagonal cross-sectional profile in its un-deployed state and a generally circular shape in its deployed state, respectively. The stent 900 includes four substantially rigid arcuate non-recessed regions 902 and four deformable, recessed regions 904 interposed between each pair of non-recessed region 902 so that the region 902 and 904 alternate. The stent 900 also includes a mechanical penetrating structure 906 deposited in valleys 908 associated with each recessed region 904. The stent's cross-sectional dimension having a first diameter $d_1$ and a second diameter or dimension $d_2$ where $d_2 \geq d_1$.

Referring now to FIG. 9C, the stent 900 is shown in perspective view where the non-recessed region 902, the recessed regions 904 and the structure 906 contained therein run parallel down a length l of the stent 900 from a first end 910 and a second end 912.

Referring now to FIGS. 9D–E, the stent 900 is shown in its undeployed and its deployed state within a vessel 914 having an interior surface or lumen 916, respectively. After deployment of the stent 900 via radial expansion, the stent's cross-sectional dimension increases to $d_2$ and as shown in FIG. 9F, the recessed regions 904, the valleys 908 and the structures 906 are elongated and flattened relative to their undeployed state and now contact and penetrate the vessel's interior 920.

Referring now to FIGS. 10A–B, an illustrative embodiment of a stent of the present invention 1000 is shown in cross-section to have a generally hexagonal cross-sectional profile in its un-deployed state and a generally circular shape in its deployed state, respectively. The stent 1000 includes four substantially rigid arcuate non-recessed regions 1002 and four deformable, recessed regions 1004 interposed between each pair of non-recessed regions 1002 so that the regions 1002 and 1004 alternate. The stent 1000 also includes a combination mechanical or electrocmechanical penetrating structure 1006 containing a composition 1007 located in protected zones 1008 associated with each recessed region 1004. The stent's cross-sectional dimension having a first diameter $d_1$ and a second diameter or dimension $d_2$ where $d_2 \geq d_1$.

Referring now to FIG. 10C, the stent 1000 is shown in perspective view where the non-recessed region 1002, the recessed regions 1004 and the structures 1006 and composition 1007 contained therein run parallel down a length l of the stent 1000 from a first end 1010 to a second end 1012.

Referring now to FIGS. 10D–E, the stent 1000 is shown in its undeployed and its deployed state within a vessel 1014 having an interior surface or lumen 1016. After deployment of the stent 1000 via radial expansion, the stent's cross-sectional dimension increases to $d_2$ and as shown in FIG. 10F, the recessed regions 1004, the protected zones 1008 and the structures 1006 containing the composition 1007 are elongated relative to their undeployed state and now penetrate the tissue or vessel's interior 1020 and delivery the bioactive agents contained within the composition 1007 into the tissue or vessel interior.

All references cited herein are incorporated herein by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A stent comprising:
    an elongate body including a protected zone including a composition, a structure or a combination of a composition and a structure,
    where the stent has an undeployed state and a deployed state,
    where the protected zone is design to deform, expand, elongate or flatten as the stent transitions from its undeployed state to it deployed state to a greater extent than the body,
    where the composition, structure or combination is substantially protected by being disposed below an undeployed outer surface of the elongate body when the stent is in its undeployed state, and
    where the composition, structure or combination after deforming, expanding, elongating or flattening becomes part of a deployed outer surface of the elongate body when the stent is in its deployed state so that the body and the protected zone of the deployed stent contact a tissue site or surface to about the same extent or so that the composition, structure or combination extends above the body contacting the tissue site or surface to a greater extent than the body.

2. The stent of claim 1, wherein the body further includes a plurality of protected zones.

3. The stent of claim 1, further comprising a plurality of alternating non-recessed and recessed regions, each recessed region comprising a protected zone.

4. The stent of claim 3, wherein the alternating non-recessed and recessed regions are oriented parallel to an axis running a length of the stent.

5. The stent of claim 3, wherein the alternating non-recessed and recessed regions comprise alternating bands oriented radially with respect to an axis running a length of the stent.

6. A stent comprising:
an elongate body and a protected zone including a composition, a structure or a combination of a composition and a structure,
where the stent has an undeployed state and a deployed state,
where the protected zone is design to deform, expand, elongate or flatten as the stent transitions from its undeployed state to it deployed state than the body,
where the composition, structure or combination is substantially protected by being disposed below an undeployed outer surface of the elongate body when the stent is in its undeployed state, and
where the composition, structure or combination after deforming, expanding, elongating or flattening becomes part of a deployed outer surface of the elongate body when the stent is in its deployed state bringing the composition, structure or combination into close proximity to or direct contact with a site in a body of an animal so that the body and the protected zone of the deployed stent contact a tissue site or surface to about the same extent or so that the composition, structure or combination extends above the body contacting the tissue site or surface to a greater extent than the body.

7. The stent of claim 6, wherein the body further includes a plurality of protected regions.

8. The stent of claim 6, further comprising a plurality of alternating non-recessed and recessed regions, each recessed region forming a protected region, where the composition and/or structure is positioned below tops of the non-recessed regions.

9. The stent of claim 8, wherein the alternating non-recessed and recessed regions are oriented parallel to an axis running a length of the stent.

10. The stent of claim 8, wherein the alternating non-recessed and recessed regions comprise alternating bands oriented radially with respect to an axis running a length of the stent.

11. A stent comprising:
a non-recessed region,
a recessed region including a composition, a structure or a combination of a composition and a structure disposed below an outer surface of the non-recessed region,
an undeployed state,
a deployed state,
where the composition, structure or combination is substantially protected by the non-recessed region when the stent is in its undeployed state, and the composition, structure or combination becomes part of an outer surface of the stent when the stent is in its deployed state and where the non-recessed region deforms to a lesser extent than the recessed regions as the stent transitions from its undeployed state to its deployed state so that the non-recessed region and the recessed region of the deployed stent contact a tissue site or surface to about the same extent or so that the composition, structure or combination extends above the body contacting the tissue site or surface to a greater extent than the non-recessed region.

12. The stent of claim 11, wherein the stent is elongate.

13. The stent of claim 11, further comprising a plurality of alternating non-recessed and recessed regions, each recessed region includes a composition, a structure or a combination disposed therein below an outer surface of its adjacent non-recessed regions and where the composition comprises a bioactive or and the structure comprises a biopenetrating agent.

14. The stent of claim 13, wherein the alternating non-recessed and recessed regions are oriented parallel to an axis running a length of the stent.

15. The stent of claim 13, wherein the alternating non-recessed and recessed regions comprise alternating bands oriented radially with respect to an axis running a length of the stent.

16. A stent comprising:
a first end;
a second end;
a first dimension when the stent is in an undeployed state;
a second dimension when the stent is in a deployed state;
two non-recessed regions, and
a recessed region interposed between the two non-recessed regions and including a composition, a structure or a combination of a composition and a structure disposed below outer surfaces of the non-recessed regions, where the non-recessed regions are adapted to protect the composition, structure or combination during stent positioning and to expose the composition, structure or combination during stent deployment bringing the composition, structure or combination into close proximity to or direct contact with a site in a body of an animal and where the non-recessed regions deform to a lesser extent than the recessed regions as the stent transitions from its undeployed state to its deployed state so that the non-recessed regions and the recessed region of the deployed stent contact a tissue site or surface to about the same extent or so that the composition, structure or combination extends above the body contacting the tissue site or surface to a greater extent than the non-recessed regions.

17. The stent of claim 16, wherein the stent is elongate.

18. The stent of claim 16, further comprising a plurality of alternating non-recessed and recessed regions, each recessed region includes a composition, a structure or a combination disposed therein below an outer surface of its adjacent non-recessed regions.

19. The stent of claim 16, wherein the alternating non-recessed and recessed regions are oriented parallel to an axis running a length of the stent.

20. The stent of claim 16, wherein the alternating non-recessed and recessed regions comprise alternating bands oriented radially with respect to an axis running a length of the stent.

21. A method for deploying a stent comprising the steps of:
positioning a stent of claims 1, 6, 11 or 16 at a site in an animals body while the stent is in its undeployed state, where the protected zone including the composition and/or structure is substantially protected; and
deploying the stent in the site so that the stent assumes its deployed state bringing the composition and/or structure into close proximity to or direct contact with to the site.

22. A method for administering a therapeutic affect to a site of an animals body comprising the steps of:
positioning a stent of claims 1, 6, 11 or 16 at a site in an animals body while the stent is in its undeployed states, where the protected zone including the composition and/or structure is substantially protected; and deploying the stent in the site so that the stent assumes its undeployed states and bringing the composition ans/or structure into close proximity to or direct contact with the site; and delivering a therapeutic affect via the composition and/or structure to the site.

* * * * *